United States Patent [19]
Henley

[11] Patent Number: 6,165,994
[45] Date of Patent: Dec. 26, 2000

[54] METHODS FOR PROMOTING THE HEALING OF CUTANEOUS WOUNDS AND ULCERS USING COMPOSITIONS OF α-D-GLUCANS

[75] Inventor: Karla J. Henley, Oak Ridge, N.C.

[73] Assignee: Blue Ridge Pharmaceuticals, Inc., Greensboro, N.C.

[21] Appl. No.: 09/246,994

[22] Filed: Feb. 8, 1999

[51] Int. Cl.$^7$ ................................................. A61K 31/715
[52] U.S. Cl. ................................................ 514/54; 514/60
[58] Field of Search ......................................... 514/54, 60

[56] References Cited

U.S. PATENT DOCUMENTS

| | | | |
|---|---|---|---|
| 4,373,519 | 2/1983 | Errede et al. | 128/156 |
| 4,818,752 | 4/1989 | Williams et al. | 514/54 |
| 4,833,131 | 5/1989 | Williams et al. | 514/54 |
| 4,975,421 | 12/1990 | Williams et al. | 514/54 |
| 5,853,749 | 12/1998 | Hobbs | 424/443 |
| 5,980,918 | 11/1999 | Klein | 424/401 |

FOREIGN PATENT DOCUMENTS 2043668  10/1980  United Kingdom .

OTHER PUBLICATIONS

Leibovich et al., Promotion of wound repair in mice by application of glucan (1980) J. Reticuloendothel. Soc. 27(1), 1–11 (abstract).

*Primary Examiner*—Kevin E. Weddington
*Attorney, Agent, or Firm*—Howrey Simon Arnold & White, LLP

[57] ABSTRACT

The present invention provides methods of promoting the healing of cutaneous wounds and ulcers in vertebrates by administering a composition of a branched chain polymeric α-D-glucan to the wound or ulcer. In a preferred embodiment, the branched chain polymeric α-D-glucan may be hetastarch. The cutaneous wound or ulcer may be an open wound or ulcer, and may be chronic. The compositions are useful for treating these wounds in vertebrates. The vertebrate may be a mammal such as a human, a canine, or any mammal. The composition utilized in the methods of the present invention may contain hetastarch.

19 Claims, No Drawings

METHODS FOR PROMOTING THE HEALING OF CUTANEOUS WOUNDS AND ULCERS USING COMPOSITIONS OF α-D-GLUCANS

BACKGROUND OF THE INVENTION

Wound healing involves a complex but orderly sequence of cellular events that culminates in the restoration of structural integrity of tissue. The orderly influx of inflammatory cells, proliferation of stromal elements, in-growth of blood vessels, and production of an extracellular matrix are essential for rapid and efficient healing. Maximum tissue strength is achieved through the regulated remodeling and maturation of the extracellular matrix. Tissue repair is regulated in part by cells at the wound site that control the local production of growth factors, including transforming growth factor beta. Wound healing begins with a repair cascade which culminates in the formation of new granulation tissue.

Cutaneous ulcers are a common, chronic problem in dogs and are primarily developed as pressure (decubital) sores. In addition to causing pain and discomfort to the animal, and predisposing the animal to superficial and chronic infection, significant costs are associated with the treatment of the animal. Certain breeds of dogs may be especially predisposed to decubital ulcers due to neurologic conditions associated with the breed. These include Dachshunds as a result of intervertebral disc herniation and large breeds such as Doberman Pinschers and Great Danes which are predisposed to cervical vertebral instability. Furthermore, any condition which results in paraplegia or tetraplegia can result in pressure ulcers.

Chronic ulcers may also arise as a result of chronic steroid therapy for autoimmune disease or atopic dermatitis as well as chemotherapy for cancer. These conditions and their treatment regimens may impair the normal wound healing process and often result in chronic ulcers in the debilitated animal. While the etiology of pressure sores or ulcers resulting from chronic steroid or chemotherapy may be different, the underlying manifestation is the lack of formation of granulation tissue and re-epithelialization of the defect. In dogs, the acral lick granuloma (acral lick dermatitis) can occur as a result of excessive licking which gradually wears away the cutaneous layers. Dehiscence wounds form as a result of failed surgical sutures. Depending on the health and background of the patient, these cutaneous open wounds and ulcers can persist chronically for extended periods of time. Each of these types of cutaneous open wounds and ulcers results in considerable discomfort to the patient and presents a continuing opportunity for even more serious infections or complications to occur. In addition to these common cutaneous open wounds and ulcers, a variety of other skin defects are known to occur in both animals and humans, including lacerations, perforations, wounds which are traumatic in origin, venous stasis ulcers, and other types of lesions.

These types of wounds also occur in other vertebrates such as birds and reptiles. The fundamental pathogenesis of wounds and processes for wound healing is similar for all vertebrates, and therefore the person of ordinary skill will realize that the methods and compositions of the present invention are useful for treating chronic wounds and ulcers in all vertebrates.

Starch is a polymer of carbohydrate moieties which are arranged in a macromolecular structure. Persons of ordinary skill in the art understand that the term "hetastarch" is meant to describe carbohydrate moieties that have been esterified so that several of the hydroxyl groups of the D-glucopyranose units of the starch polymer have been converted into hydroxyethyl groups. Hetastarch is commonly utilized in preparations of plasma volume expanders to avoid the potentially fatal shock which can result from severe blood loss, particularly in cases where the treated patient has experienced a large volume of blood loss. These hetastarch compositions are considered a safer alternative to blood products as their use avoids the possibility of transmitting blood-borne diseases. They are also useful for treating patients who object to blood products for resuscitation and when donor blood is unavailable or available in insufficient quantities. Hetastarch compositions are also significantly less expensive than donated blood.

Hetastarch is also known in the art as hydroxyethylated amylopectin, hydroxyethyl starch, or generally as a branched chain polymeric α-D-glucan. The term hetastarch as used herein is meant to include these and any other terms known in the art as describing branched chain polymeric α-D-glucans which have been esterified so that several of the hydroxyl groups of the D-glucopyranose units of the starch polymer have been converted into hydroxyethyl groups.

The present invention resulted from the unexpected discovery that compositions containing hetastarch are also useful for promoting the healing of cutaneous open wounds and ulcers. In a recent study it was unexpectedly found that chronic open wounds and ulcers in dogs treated with a composition of hetastarch healed as well as chronic open wounds and ulcers treated with a known biochemical wound healing agent.

SUMMARY OF THE INVENTION

The present invention provides methods of promoting the healing of cutaneous wounds and ulcers in vertebrates. The methods include the step of administering a composition containing a branched chain polymeric α-D-glucan to the cutaneous wound or ulcer. In a preferred embodiment, the cutaneous wound or ulcer may be a cutaneous open wound or ulcer, and may also be chronic, and the branched chain polymeric α-D-glucan may be hetastarch. In particularly preferred embodiments, the cutaneous open wound or ulcer may be a cutaneous open wound or ulcer and may be a decubital ulcer, a dehiscence wound, an acral lick dermatitis (acral lick granuloma), a laceration, a traumatic wound, a venous stasis ulcer, or another type of lesion. The cutaneous open wound or ulcer may occur in a mammal, and the mammal may be a human, a canine, a feline, a bovine, an ovine, an equine, a porcine, or any mammal. The present invention may be practiced with compositions containing hetastarch. In various embodiments, the present invention may be practiced with compositions containing at least 25 percent of a branched chain polymeric α-D-glucan, such as hetastarch. In a preferred embodiment, the composition may contain from about 40% to about 70% (w/v) hetastarch. In a more preferred embodiment, the hetastarch composition may contain about 50% (w/v) hetastarch. In other embodiments, the composition may additionally contain about 20 mM sodium acetate or another suitable buffer.

DETAILED DESCRIPTION OF THE INVENTION

The present invention provides methods of promoting the healing of cutaneous open wounds and ulcers including the step of administering a branched chain polymeric α-D-glucan to the open wound or ulcer. In a preferred embodiment, the branched chain polymeric α-D-glucan composition may be hetastarch. The present invention is useful for treating any type of cutaneous open wounds or ulcers. In a preferred embodiment, the cutaneous open wound or ulcer will be a chronic open wound or ulcer. In particularly preferred embodiments, the open wound will be an acral lick dermatitis (acral lick granuloma), a decubital ulcer, a laceration, a traumatic wound, a post-surgical dehiscence wound, a perforation, or another type of lesion such as a venous stasis ulcer or a common surgical suture.

The composition utilized in the present invention may contain a branched chain polymeric α-D-glucan and the polymeric α-D-glucan may be hetastarch. At least some wound healing properties are obtainable with compositions containing any amount of hetastarch, even 10% or 5% (w/v), or less. The hetastarch composition used in the present invention may more favorably comprise at least 25% hetastarch (w/v). In a preferred embodiment, the composition of the present invention may contain from about 40% to about 70% (w/v) hetastarch. In a particularly preferred embodiment, the composition of the present invention may comprise about 50% (w/v) hetastarch. The hetastarch compositions utilized in the present invention may also contain about 20 mM sodium acetate or another suitable buffer at a suitable concentration, and may further comprise benzethonium chloride or any quaternary ammonium compound or any other suitable preservative, and may also contain polysorbate 80 or another suitable non-ionic surfactant.

The composition has been used with success in treating cutaneous open wounds and ulcers in canines. The treatment may involve covering the surface of the open wound or ulcer every three to four days with the hetastarch composition. The application of a bandage to the wound is optional.

The person of ordinary skill will realize that the present invention may also be usefully practiced with any branched chain polymeric α-D-glucan. For example, other starches based on polymeric hexose units will be useful in practicing the present invention. Polymers containing pentose, such as that known as pentastarch, may also be useful in practicing the present invention. More particularly, branched chain polymers containing pentose may be useful in practicing the present invention.

By "open wound" is meant any injury which communicates with the atmosphere by direct exposure. Open wounds include, but are not limited to, decubital ulcers, dehiscence wounds, acral lick dermatitis (acral lick granulomas), lacerations, and wounds that are traumatic in origin.

By "ulcer" is meant a break in the continuity of the epidermis with a loss of substance and exposure of underlying tissue.

By "chronic cutaneous open wound or ulcer" is meant a cutaneous open wound or ulcer which has shown resistance to completing the healing process.

The invention is further illustrated in the following examples. These examples are not intended to be limiting. The person of ordinary skill in the art will realize that these methods and compositions can be applied to treat a variety of open wounds and ulcers in a variety of mammals including humans, canines, felines, bovines, felines, ovines, equines, porcines and may be applied to birds, reptiles, and other vertebrates as well.

EXAMPLE 1

Several dogs were used in the study of various ages, breeds, weights, and physiological states. Approximately one-half of the dogs used in the study were male and approximately one-half were female. Each dog presented with a difficult to heal or non-healing cutaneous open wound or ulcer that did not exceed 25 $cm^2$ in surface area.

The dogs were dosed with approximately 1 ml per 25 $cm^2$ of wound area of a composition of 50% hetastarch (w/v) every four days as a thin coat on the surface of the fresh granulation tissue. Generally, a wound approximately the size of a quarter received 3 drops and a wound approximately the size of a half-dollar received 4 drops. The hetastarch compound was administered topically following gentle debridement or at least freshening of the wound or ulcer to remove fibrin deposits, fibrous tissue, necrotic tissue, and foreign material. The wound or ulcer bed consisted of fresh granulation tissue that was oozing blood and serum. Some wounds or ulcers were bandaged, while others were left uncovered. The following example cases illustrate some of the results which were obtained by using the compositions and methods of the present invention. These results are typical and are intended only as representative examples of results which have been achieved using the compositions and methods of the present invention.

Case 1

A seven year old Doberman Pinscher, castrated male, 95 lbs presented with a lick granuloma on the right metatarsal area which had been present for more than one year. The wound area was 16.2 $cm^2$. Treatment consisted of applying approximately 0.7 ml of hetastarch formulation every four days without bandaging. The wound was completely healed in 28 days.

Case 2

A 3.5 year old Fox Terrier mix, castrated male, 41.1 lbs presented with a tramautic wound to the left shoulder inflicted by a dog bite. The wound had been present for two months prior to presentation. Surgical closure was attempted one month after the initial injury, but a 2.77 $cm^2$ area of the suture line still was not healed at the time of presentation. Treatment consisted of the application of approximately 0.2 ml of hetastarch formulation every four days without bandaging. The wound completely healed in 50 days.

Case 3

The patient was a seven year old Mixed Breed, spayed female, 102 lbs. A lick granuloma on the right distal antebrachium had been surgically removed 1.5 years prior to presentation. The wound had never healed properly following the surgery, and the area was 1.89 $cm^2$ at the initiation of treatment. Treatment consisted of the application of approximately 0.1 ml of hetastarch formulation every four days without bandaging. The wound area decreased to 0.63 $cm^2$ after 56 days of therapy.

Case 4

The patient was a 1.5 year old Jack Russell Terrier, male, 18.4 lbs which sustained a degloving injury of the right carpus/metacarpus when hit by a car. The wound granulated in, but never epithelialized. The injury had occurred five weeks prior to presentation and was 1.88 $cm^2$. Treatment consisted of the application of approximately 0.1 ml of hetastarch formulation every four days, followed by bandaging. The wound completely healed in eight days after only two applications of hetastarch formulation.

Case 5

The patient was an eight year old, Basset Hound, male, 52.7 lbs. with a non-healing wound on the ventral neck which had been present for three weeks prior to presentation. The wound area was 4.31 $cm^2$ at the time of presentation. Treatment consisted of the application of approximately 0.2 ml of hetastarch formulation every four days without bandaging. The wound completely healed in 14 days.

Case 6

The patient was a five year old, Mixed Breed, male, 14.25 lbs which had experienced an episode of heat stroke three weeks prior to presentation. The heat stroke had created multiple areas of full thickness skin necrosis and resulting open wounds. At presentation, there was one wound with an area of 2.22 cm$^2$ that had not healed. Treatment consisted of the application of approximately 0.1 ml of hetastarch formulation every four days without bandaging. The wound completely healed in 28 days.

Case 7

A 5.5 year old German Shepherd, spayed female, 66 lbs presented with a non-healing wound on the bottom of the right paw. The wound had been present for three years and had an area of 3.34 cm$^2$ at the time of presentation. Treatment consisted of the application of approximately 0.2 ml of hetastarch formulation every four days without bandaging. The wound had decreased to an area of 0.45 cm$^2$ in 56 days.

What is claimed is:

1. A method of promoting the healing of cutaneous wounds and ulcers in vertebrates comprising:

administering an α-D-glucan composition to the cutaneous wound or ulcer.

2. The method of claim 1 wherein the αD-glucan is a branched chain polymeric α-D-glucan.

3. The method of claim 2 wherein the cutaneous wound or ulcer is a cutaneous open wound or ulcer.

4. The method of claim 2 wherein the branched chain polymeric α-D-glucan is hetastarch.

5. The method of claim 3, wherein the cutaneous open wound or ulcer is selected from the group consisting of: a decubital ulcer, a dehiscence wound, an acral lick dermatitis, a laceration, and a traumatic wound.

6. The method of claim 3 wherein the cutaneous open wound or ulcer is a venous stasis ulcer.

7. The method of claim 3, wherein the cutaneous open wound or ulcer is a chronic cutaneous open wound or ulcer.

8. The method of claim 3 wherein the composition comprises at least about 25 percent hetastarch.

9. The method of claim 3 wherein the composition comprises at least about 5 percent hetastarch.

10. The method of claim 3 wherein the composition comprises from about 40 percent to about 70 percent hetastarch.

11. The method of claim 10 wherein the composition comprises about 50 percent hetastarch.

12. The method of claim 10 wherein the composition further comprises about 20 mM sodium acetate.

13. The method of claim 5 wherein the branched chain polymeric α-D-glucan is hetastarch.

14. The method of claim 5 wherein the vertebrate is a mammal.

15. The method of claim 14 wherein the mammal is a canine.

16. The method of claim 14 wherein the mammal is a human.

17. The method of claim 14 wherein the mammal is selected from the group consisting of a bovine, a feline, an ovine, an equine, and a porcine.

18. A method of promoting the healing of cutaneous wounds and ulcers in vertebrates comprising:

administering a composition containing a polymer of pentose to the cutaneous wound or ulcer.

19. The method of claim 18 wherein the polymer of pentose is a branched chain polymer of pentose.

* * * * *